(12) United States Patent
Langer et al.

(10) Patent No.: US 10,238,885 B2
(45) Date of Patent: Mar. 26, 2019

(54) OUTPATIENT HEALTH EMERGENCY WARNING SYSTEM

(71) Applicant: HEALTH ALERT, LLC, Boise, ID (US)

(72) Inventors: Alois Antonin Langer, Harrison City, PA (US); Walter Louis Seale, Boise, ID (US)

(73) Assignee: Health Alert, LLC, Boise, ID (US)

( * ) Notice: Subject to any disclaimer, the term of this patent is extended or adjusted under 35 U.S.C. 154(b) by 754 days.

(21) Appl. No.: 13/862,947

(22) Filed: Apr. 15, 2013

(65) Prior Publication Data

US 2013/0274565 A1 Oct. 17, 2013

Related U.S. Application Data

(60) Provisional application No. 61/686,883, filed on Apr. 13, 2012.

(51) Int. Cl.
*A61N 1/39* (2006.01)
*A61B 5/0402* (2006.01)
(Continued)

(52) U.S. Cl.
CPC .......... *A61N 1/3993* (2013.01); *A61B 5/0004* (2013.01); *A61B 5/0205* (2013.01); *A61B 5/02438* (2013.01); *A61B 5/02455* (2013.01); *A61B 5/0402* (2013.01); *A61B 5/1118* (2013.01); *A61B 5/681* (2013.01); *A61B 5/6823* (2013.01); *A61B 5/6824* (2013.01);
(Continued)

(58) Field of Classification Search
None
See application file for complete search history.

(56) References Cited

U.S. PATENT DOCUMENTS 4,023,673 A   5/1977   Pantridge et al.
4,102,332 A   7/1978   Gessman
(Continued)

FOREIGN PATENT DOCUMENTS

EP   0459239   5/1991
EP   2298164   9/2010
(Continued)

OTHER PUBLICATIONS

International Search Report and Written Opinion, PCT/US2013/036509, dated Jul. 18, 2013.
(Continued)

*Primary Examiner* — Niketa Patel
*Assistant Examiner* — Qingjun Kong
(74) *Attorney, Agent, or Firm* — Stoel Rives LLP

(57) ABSTRACT

A medical system for sensing a physiological state requiring defibrillation in a patient. The system comprising: a low power sensor, a physiological parameter measuring device, and a processor. The low power sensor generating a baseline signal relating to a physiological status of said patient. The physiological parameter measuring device comprising at least one higher power sensor configured to output at least one physiological parameter signal indicative of at least one physiological parameter of said patient. The processor assessing the baseline signal and determining if the physiological status is outside predetermined threshold boundaries.

11 Claims, 7 Drawing Sheets

(51) Int. Cl.
*A61B 5/00* (2006.01)
*A61B 5/024* (2006.01)
*A61B 5/11* (2006.01)
*A61B 5/0245* (2006.01)
*A61B 5/0205* (2006.01)

(52) U.S. Cl.
CPC ...... *A61B 5/746* (2013.01); *A61B 2562/0219* (2013.01); *A61B 2562/06* (2013.01); *A61N 1/3925* (2013.01)

(56) References Cited

U.S. PATENT DOCUMENTS

| | | | |
|---|---|---|---|
| 4,202,340 | A | 5/1980 | Langer et al. |
| 4,928,690 | A | 5/1990 | Heilman et al. |
| 5,645,571 | A | 7/1997 | Olson et al. |
| 6,292,687 | B1* | 9/2001 | Lowell .................. A61B 5/1112 600/515 |
| 8,255,051 | B2 | 8/2012 | Cholette |
| 8,271,072 | B2 | 9/2012 | Houben et al. |
| 8,369,936 | B2 | 2/2013 | Farringdon et al. |
| 2003/0153836 | A1* | 8/2003 | Gagnadre .......... A61B 5/02055 600/483 |
| 2007/0276270 | A1* | 11/2007 | Tran .................... A61B 5/0022 600/508 |
| 2008/0312709 | A1* | 12/2008 | Volpe .................. A61B 5/0404 607/6 |
| 2009/0069642 | A1 | 3/2009 | Gao et al. |
| 2010/0261980 | A1* | 10/2010 | Peng .................. G08B 21/0446 600/301 |
| 2012/0215123 | A1 | 8/2012 | Kuman et al. |
| 2013/0030259 | A1 | 1/2013 | Thomsen et al. |

FOREIGN PATENT DOCUMENTS

| | | |
|---|---|---|
| RU | 2378983 C1 | 1/2010 |
| RU | 2444986 C1 | 3/2012 |
| WO | 9839061 | 9/1998 |
| WO | 2004030756 | 4/2004 |
| WO | 2004084720 | 10/2004 |
| WO | 2005106813 | 10/2005 |
| WO | 2006065679 | 6/2006 |
| WO | 2006076498 | 7/2006 |
| WO | 2006109072 | 10/2006 |
| WO | 2006119345 | 11/2006 |
| WO | 2007072425 A2 | 6/2007 |
| WO | 2007126955 | 11/2007 |

OTHER PUBLICATIONS

Montague, Shannon Wolf, "Optimising the National Health Service Through Remote Vital Sign Monitoring: zensor," Intelesens Remote Healthcare, Jan. 2013.

Lin, Bin, et al., "Electrical, Rheological, and Mechanical Properties of Polystyrene/Copper Nanowire Nanocomposites," Ind. Eng. Chem. Res., 2007, 2481-87.

* cited by examiner

US 10,238,885 B2

OUTPATIENT HEALTH EMERGENCY WARNING SYSTEM

PRIORITY/CROSS-REFERENCE TO RELATED APPLICATIONS

This application claims the benefit of U.S. Provisional Application No. 61/686,883, filed 13 Apr. 2012.

DESCRIPTION

Figure 1:
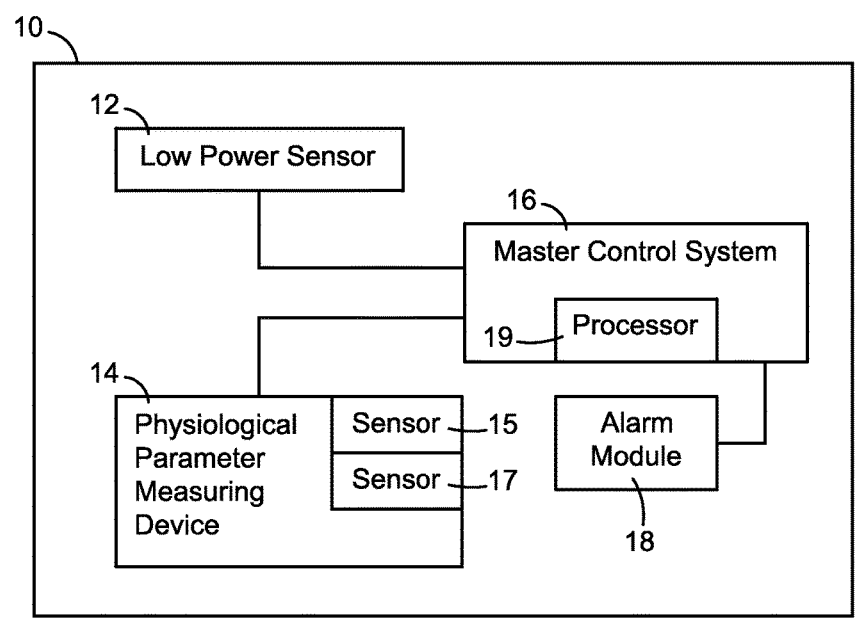
FIG. 1 is a diagram of an embodiment of a medical system.

The following description and the referenced drawings provide illustrative examples of the inventors' outpatient health emergency warning system. As such, the embodiments discussed herein are merely exemplary in nature and are not intended to limit the scope of the outpatient health emergency warning system, or its protection, in any manner. Rather, the description and illustration of these embodiments serve to enable a person of ordinary skill in the relevant art to practice embodiments of the outpatient health emergency warning system.

The use of "e.g.," "etc.," "for instance," "for example," and "or" and grammatically related terms indicates non-exclusive alternatives without limitation, unless otherwise noted. The use of "including" and grammatically related terms means "including, but not limited to," unless otherwise noted. The use of the articles "a," "an" and "the" are meant to be interpreted as referring to the singular as well as the plural, unless the context clearly dictates otherwise. Thus, for example, reference to "a sensor" includes two or more such sensors, and the like. The use of "optionally," "alternatively," and grammatically related terms means that the subsequently described element, event or circumstance may or may not be present/occur, and that the description includes instances where said element, event or circumstance occurs and instances where it does not. The use of "preferably" and grammatically related terms means that a specified element or technique is more acceptable than another, but not that such specified element or technique is a necessity, unless the context clearly dictates otherwise. The use of "exemplary", means "an example of" and is not intended to convey a meaning of an ideal or preferred embodiment.

The use of "sensor" means any device that performs a measurement of its environment and transmits a signal regarding that measurement, including but not limited to, capacitive sensors, proximity sensors, switches, buttons, sound/voice control sensors, RFID, infrared, accelerometers, and gyroscopes, unless the context clearly dictates otherwise.

The use of "motion sensor" means any device that measures motion and transmits a motion signal, including but not limited to accelerometers, and gyroscopes, unless the context clearly dictates otherwise.

The use of "wireless connection" means any wireless signal, data, communication, or other interface including without limitation WiFi, Bluetooth, RF, ZIGBEE, ANT, acoustic, and infrared, unless the context clearly dictates otherwise.

The use of "memory" means any type of long term, short term, volatile, nonvolatile, or other storage devices and is not to be limited to any particular type of memory or number of memories, or type of media upon which memory is stored, including but not limited to random access memory (RAM) or other dynamic storage device (e.g., dynamic RAM (DRAM), and static RAM (SRAM), synchronous DRAM (SDRAM), flash RAM), unless the context clearly dictates otherwise.

The use of "computer readable media" means any medium that participates in providing instructions to a processor for execution, including but not limited to hard disks, floppy disks, tape, magneto-optical disks, PROMs (EPROM, EEPROM, Flash EPROM), DRAM, SRAM, SDRAM, or any other magnetic medium, magneto-optical disks, compact disks (e.g., CD-ROM), laser disc, digital versatile disc (DVD), Blu-ray disc, or any other optical medium, punch cards, paper tape, or other physical medium with patterns of holes, a carrier wave (described below), or any other medium from which a computer can read, and combinations of the above, unless the context clearly dictates otherwise.

The use of "control logic" applies to software (in which functionality is implemented by instructions stored on a machine-readable medium to be executed using a processor), hardware (in which functionality is implemented using circuitry (such as logic gates), where the circuitry is configured to provide particular output for particular input, and firmware (in which functionality is implemented using re-programmable circuitry), and also applies to combinations of one or more of software, hardware, and firmware, unless the context clearly dictates otherwise.

The use of "processor" means a programmable system including systems and microcontrollers, reduced instruction set circuits (RISC), application specific integrated circuits (ASIC), programmable logic circuits (PLC), and any other circuit capable of executing the functions described herein, including but not limited to microprocessors, digital signal processors, analog processors, analog devices (e.g., switched capacitors), analog/digital logic circuits, discrete transistors, integrated circuits, and many other devices can be used to perform such processing, unless the context clearly dictates otherwise.

FIG. 1 illustrates a first medical system 10 for sensing a physiological state requiring defibrillation in a patient, for instance asystole or ventricular fibrillation. The medical system 10 having a low power sensor 12, physiological parameter measuring device 14, a master control system 16, and alarm module 18.

The low power sensor 12 is for generating a baseline signal relating to a status of said patient, the baseline signal for initially predicting whether or not the patient may be having cardiac problems. For instance, in one embodiment, the low power sensor 12 can comprise a motion sensor, such as an accelerometer, for sensing whether the patient has ceased movement, the motion sensor generating a motion signal relating to the activity level of the patient. In another embodiment, the low power sensor 12 comprises an electrocardiogram (ECG) sensor for sensing the electrical activity of the patient's heart over a period of time via electrodes attached to the surface of the patient's skin. Any suitable sensor may be utilized as the low power sensor 12.

The physiological parameter measuring device is 14 for measuring at least one physiological parameter of the patient. The physiological parameter measuring device 14 comprising at least one physiological parameter sensor 15. Such a physiological parameter sensor 15 may have higher power consumption than the low power sensor 12. In some embodiments, the physiological parameter sensor 15 has the ability to be placed into a low power state, put to sleep, and be awakened by some event, for instance by the low power sensor detecting a potential exceptional condition is present.

The physiological parameter sensor 15 performs sensing operations. To conserve battery power, when not performing sensing operations, the physiological parameter sensor 15 sleeps or enters into another low power state (collectively referred to herein as a "low power state"). In some embodiments, the control logic (discussed infra) can cause the physiological parameter sensor 15 to enter into the low power state, for instance, the master control system 16 can send a signal to the physiological parameter sensor 15 instructing the physiological parameter sensor 15 to enter the low power state.

When the physiological parameter sensor 15 is not in the low power state, the physiological parameter sensor 15 acquires sensor data. The physiological parameter sensor 15 can analyze the sensor data to determine whether an exceptional condition, such as a threshold being exceeded, is present, and/or the physiological parameter sensor 15 can relay the sensor data to another component, for instance the master control system 16, which can analyze the sensor data to determine whether an exceptional condition, such as a threshold being exceeded, is present.

The physiological parameter sensor 15 is configured to output at least one physiological parameter signal indicative of at least one physiological parameter of the patient. The physiological parameter sensor(s) can comprise any suitable physiological parameter sensor, including but not limited to ECG sensors, blood oxygen sensors, heart pulse sensors, pulse oximeters, and a temperature sensors. The physiological parameter measuring device 14 may comprise multiple physiological parameter sensors located together in a central housing, for instance sensor 15 and sensor 17 illustrated in FIG. 1.

The physiological parameter sensor 15 is configured for placement adjacent the patient's skin interface, for allowing the physiological parameter sensor 15 to sense the patient's physiological status. In some embodiments, at least part of the physiological parameter measuring device 14 is disposed in a housing worn on at least one of the patient's wrists, or in a housing attached to a chest strap worn by the patient. Alternatively, the physiological parameter sensor 15 itself could be configured for wearing against the skin of the patient, for instance as a self-adhesive pad.

The master control system 16 is for controlling the operation of the medical system 10. The master control system 16 comprising a processor 19 for assessing the baseline signal. The processor 19 implementing at least in part control logic for determining if the patient's physiological status is below a threshold level or outside of certain normal boundaries. Whereupon determining that the physiological status may be below said threshold level or outside of the boundaries, the control logic is configured to wake up the physiological parameter measuring device 14 and/or physiological parameter sensor 17 and/or other sensors. Upon waking up, the sensor 15 and/or sensor 17 acquiring a physiological parameter signal indicative of at least one physiological parameter of the patient. In other embodiments, the processor and the sensor are integrated together.

The processor 19 of the master control system 16 assessing the at least one physiological parameter signal to determine whether a physiological state requiring defibrillation in the patient is present. If it is determined that a physiological state requiring defibrillation in the patient is present, the processor 19 outputs an alarm signal to alarm module 18.

The alarm module 18 for generating an alarm signal. The term alarm module including all devices usable with a medical system that are suitable for giving an alarm or a warning, including but not limited to an amplifier and a speaker, a beeper, or another device capable of making sound. The alarm signal may comprise an audible alarm indicating to a third party, such as a medical or non-medical caretaker, that the patient is experiencing emergency level physiological parameters and an external free-standing defibrillator needs to be utilized on said patient. The alarm module 18 can be worn by the patient, or can be remote from the patient. Further, a wireless connection can be utilized to connect a remote alarm module to the medical system.

The medical system can further comprises an external, free-standing defibrillator for use by a third party in response to said alarm.

Figure 2:
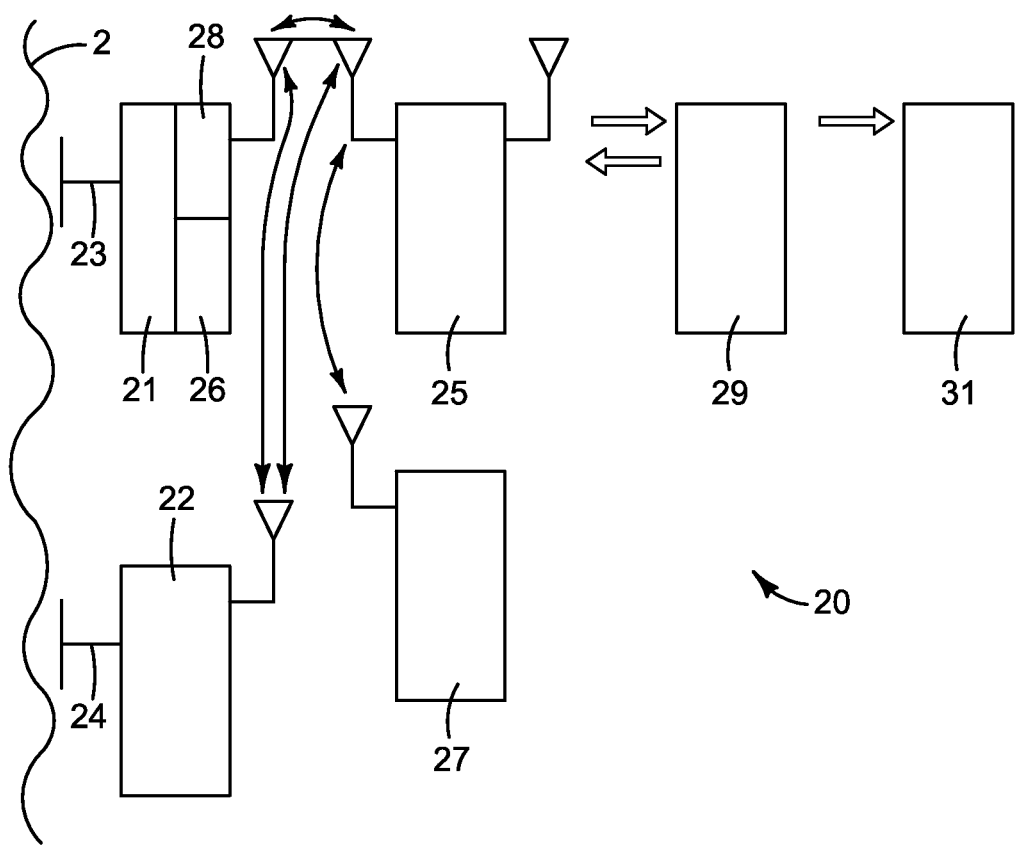
FIG. 2 is a diagram of a second embodiment of a medical system.

The medical system could further comprise multiple physiological parameter measuring devices, each with one or more physiological parameter sensors. For instance, as illustrated in FIG. 2, a second medical system 20 for sensing a physiological state requiring defibrillation in a patient is illustrated. The medical system 20 having a first physiological parameter measuring device 21 including a low power sensor 26, and a master control system 28; a second physiological parameter measuring device 22; alarm module 27; a central receiver station 29; and Emergency Medical Services 31.

The low power sensor 26 is integrated into the physiological parameter measuring device 21, and is for generating a baseline signal relating to a status of said patient, the baseline signal for initially predicting whether or not the patient may be having cardiac problems. For instance, in one embodiment, the low power sensor 26 can comprise a motion sensor, such as an accelerometer, for sensing whether the patient has ceased movement, the motion sensor generating a motion signal relating to the activity level of the patient. In another embodiment, the low power sensor 26 comprises an electrocardiogram (ECG) sensor for sensing the electrical activity of the patient's heart over a period of time via electrodes attached to the surface of the patient's skin. Any suitable sensor may be utilized as the low power sensor 26.

The first physiological parameter measuring device 21 and the second physiological parameter measuring device 22 are for measuring at least one physiological parameter of the patient. In one embodiment, the first physiological parameter measuring device 21 and the second physiological parameter measuring device 22 each comprise at least one physiological parameter sensor (23, 24). In other embodiments, at least one of the physiological parameter measuring devices may include multiple physiological parameter sensors. The physiological parameter measuring devices could include the same physiological parameter sensors, could include some of the same physiological parameter sensors, or could include none of the same physiological parameter sensors.

Such physiological parameter sensors 23, 24 may have higher power consumption than the low power sensor 26. In some embodiments, the physiological parameter sensors 23, 24 have the ability to be placed into a low power state, put to sleep, and be awakened by some event, for instance by the low power sensor 26 detecting a potential exceptional condition is present.

As illustrated in FIG. 2, the first physiological measuring device 21 and the second physiological measuring device 22, and the sensors associated therewith, are located separately, thereby enabling them to be spaced apart if so desired. For instance, multiple physiological parameter measuring devices and/or sensors can be distributed on the patient's body depending on the physiological parameter to be sensed (e.g., ECG electrodes).

The physiological parameter sensors 23, 24 perform sensing operations. To conserve battery power, when not performing sensing operations, the physiological parameter sensors 23, 24 sleep or enter into another low power state (collectively referred to herein as a "low power state"). In some embodiments, the control logic (discussed infra) can cause one or both of the physiological parameter sensors 23, 24 to enter into the low power state, for instance, the master control system 28 can send a signal to one or both of the physiological parameter sensors 23, 24 instructing it/them to enter the low power state. While in this Figure the master control system 28 is illustrated as being integrated into the physiological parameter measuring device 21, in other embodiments it could be located within another module, or within a separate module.

When the physiological parameter sensors 23, 24 are not in the low power state, the physiological parameter sensors 23, 24 acquire sensor data. The physiological parameter sensors 23, 24 can analyze the sensor data to determine whether an exceptional condition, such as a threshold being exceeded, is present, and/or the physiological parameter sensors 23, 24 can relay the sensor data to another component, for instance the master control system 28, which can analyze the sensor data to determine whether an exceptional condition, such as a threshold being exceeded, is present.

In some embodiments, the physiological parameter sensors 23, 24 are each configured to output at least one physiological parameter signal indicative of at least one physiological parameter of the patient. The physiological parameter sensor(s) can comprise any suitable physiological parameter sensor, including but not limited to ECG sensors, blood oxygen sensors, heart pulse sensors, a pulse oximeters, and a temperature sensors. The physiological parameter measuring devices 21, 22 may comprise multiple physiological parameter sensors located together in a central housing.

In some embodiments, the physiological parameter sensors 23, 24 are configured for placement adjacent the patient's skin interface, for allowing the physiological parameter sensors 23, 24 to sense the patient's physiological status. In some embodiments, at least part of the physiological parameter measuring device 21, 22 is disposed in a housing worn on at least one of the patient's wrists, or in a housing attached to a chest strap worn by the patient. Alternatively, ate least one of the physiological parameter sensors 23, 24 could be configured for wearing against the skin of the patient, for instance as a self-adhesive pad. In other embodiments, none of the components/modules are worn on the patient's body.

The master control system 28 is for controlling aspects of the operation of the medical system 20. The master control system 28 in this embodiment is integrated into the physiological parameter measuring device 21. The master control system 28 comprising a processor for assessing the baseline signal. The processor implementing at least in part control logic for determining if the patient's physiological status is below a threshold level. Whereupon determining that the physiological status may be below said threshold level, the control logic is configured to wake up at least one of the physiological parameter measuring devices 21, 22, and/or at least one of the physiological parameter sensors 23, 24 and/or other sensors. Upon waking up, the physiological parameter sensor(s) acquire a physiological parameter signal indicative of at least one physiological parameter of the patient. In other embodiments, the processor and the sensor are integrated together. In another embodiment, the master control system 28 is integrated into the communication device 25 instead of the physiological parameter measuring device 21, or another module.

In another embodiment, the master control system has an active mode, a sleep mode, and an interrupt system. In such an embodiment, the master control system operates in a sleep (low power) mode until an interrupt signal is received, at which time the master control system "wakes up." In one such embodiment, the master control system's default mode is the sleep mode. In sleep mode, the master control system utilizes less power. The low power sensor is configured to monitor the physiological status, and upon sensing a physiological status outside of boundary conditions issue an interrupt signal to the master control system, triggering the master control system to enter into the active mode. For instance, in an embodiment including a motion sensor, such as an accelerometer, when the patient's movements are above a certain threshold, the accelerometer (or other module) could send an interrupt signal to the processor thereby interrupting the sleep mode. At that point, the master control system can determine whether the physiological parameter is within normal limits, and if so can re-enter sleep mode. If the physiological parameter is not within normal limits, the master control system could initiate other action.

In another embodiment, the master control system has an active mode, a sleep mode, and an interrupt system. The low power sensor implements control logic for determining if the physiological status is outside predetermined threshold boundaries. If the control logic determines that the physiological status is outside the threshold boundaries, the control logic causes an interrupt signal to be issued to the master control system, triggering the master control system to enter into the active mode.

The processor of the master control system 28 assessing the at least one physiological parameter signal to determine whether a physiological state requiring defibrillation in the patient is present. If it is determined that a physiological state requiring defibrillation in the patient is present, the master control system 28 outputs an alarm signal to alarm module 27 and/or to communication device 25 (e.g., cell phone).

The alarm module 27 for generating an alarm signal. The alarm module 27 can comprise an amplifier and a speaker, where the alarm signal is an audible alarm indicating to a third party that the patient is experiencing emergency level physiological parameters and an external free-standing defibrillator needs to be utilized on said patient.

The alarm module 27 and/or the master control system 28 can further comprise a communication device for communicating at least one of said signals to a central receiving station 29. The central receiving station 29 could comprise an emergency level verification system for verifying said signal(s) to determine if emergency level physiological parameters are present. The central receiving station 29 could further comprise a confirmation signal generator for generating a confirmation signal upon the verification of the presence of emergency level physiological parameters. The master control system 28 could be configured to receive the confirmation signal and for automatically providing notice of the detection of an emergency-level physiological parameter to a third party proximal to the patient. The master control system 28 indicating to said third party that the individual is experiencing emergency level physiological parameters and the external free-standing defibrillator needs to be utilized on said individual. In some embodiments, the central receiving station 29 contacts emergency medical services 31 regarding the emergency.

FIG. 2 illustrates the various components of the medical system 20 wirelessly connected with one another. Alternatively, one or more of the connections can be a wired connection. As illustrated in FIG. 2, a wireless connection could be utilized enabling the components to communicate by radio through a small Personal Area Network (PAN) using a convenient protocol. Such networks are known in the art and some examples include, but are not limited to, the ZigBee protocol, the ANT protocol, or Bluetooth. In some embodiments, the master control system 28 could comprise a cell phone, or a fully custom wireless signal processing module as part of the PAN.

At least one of the physiological parameter sensors 23, 24 and/or at least one of the physiological parameter measuring devices 21, 22 can pre-processes the physiological parameter signal for alarm levels, and/or can transmit pre-processed physiological data to a another module for further signal analysis. Preprocessing may include conversion of the physiological parameter to an electrical signal, filtering, analog to digital conversion, digital filtering and other steps.

In the embodiment illustrated in FIG. 2, the physiological parameter measuring device 21 comprises one or more sensors. Such sensors potentially including, but not limited to, the low power sensor 26 (e.g., a motion sensor), an IR pulse sensor, an ECG sensor, and a temperature sensor.

Upon detecting an alarm condition, the physiological parameter measuring device 21 and/or the master control system 28 can transmit an alert signal, and optionally sample physiological data to communication device 25 (e.g., a cell phone). The communication device 25 can transmit the alarm over a network, such as the cellular system, and through the Internet to a central receiver station 29. Upon detection of an alarm condition, the central receiver station 29 can access patient information in a database and optionally dispatch Emergency Medical Services 31, if needed.

In some embodiments, the signal processing steps are distributed among the various modules in the medical system.

In some embodiments, the physiological parameter sensors can each transmit pre-processed physiological data to the communication device 25, which runs various algorithms to sense alarm levels in the physiological parameters. The communication device 25 can send physiological or alert data to the central receiver station 29, thereby distributing at least some of the signal processing steps to separate devices.

The medical system 20 includes an alarm module 27. Upon sensing an alarm condition, a signal is received by the alarm module 27 prompting an alarm. Examples of alarms include, but are not limited to, audio alarms, video alarms, audio/visual alarms, and message alarms transmitted remotely to a caregiver's electronic device (e.g., pager, cell phone).

Figure 3:
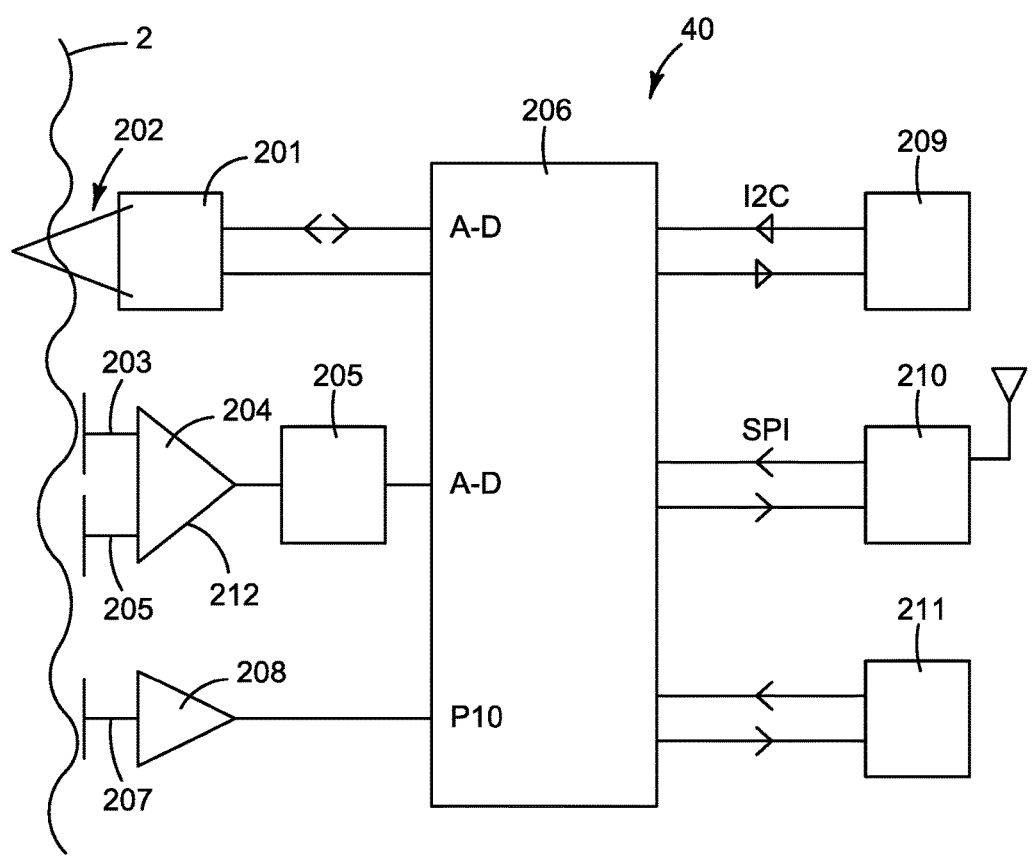
FIG. 3 is a diagram of am embodiment of a physiological parameter measuring device.

FIG. 3 illustrates another embodiment of a physiological parameter measuring device 40. This embodiment of a physiological parameter measuring device 40 configured for wearing on the wrist of a patient, for instance as a watch or bracelet. One embodiment having a housing with at least one strap or band extending therefrom. In the illustrated physiological parameter measuring device 40, all of the sensors could be contained within a single housing.

The physiological parameter measuring device 40 illustrated in FIG. 3 comprising an optical sensor 201, an ECG sensor 204, analog pre-processing module 205, touch switch 207, a low power sensor 209, temperature sensor 211, and processor 206.

The optical sensor 201 serves as a heart pulse sensor based on one or more light emitting diodes (LEDs) and a photodiode somewhat similar to what is used in a pulse oximeter. The optical sensor 201 can be used to sense blood oxygenation levels ($SpO_2$). One embodiment of an optical sensor 201 comprises a light source 202 (e.g., a light-emitting diode (LED) module), light drivers configured for driving the LED(s) at a narrow constant current pulse, and photodiodes or in the alternative, phototransistors, which receive scattered light from the patient's tissue including blood. The amount of scattered light varies with tissue oxygenation resulting in received light amplitude which varies with the patient's heartbeat. The photodiodes or transistors are connected to an amplifier which is designed to respond to narrow light pulses in order to save power. The optical sensor 201 is adapted to determine whether a heart pulse is still present. In other words, during times of ventricular fibrillation, the pulse in the received light intensity waveform will not be present and this absence is indicative absent perfusion such as in ventricular fibrillation, ventricular tachycardia, or other cases of cardiac arrest.

One component with a potentially significant current (power) draw is/are the LED(s) used in the system. To produce useful light intensity, a LED must be driven with perhaps 10's of milli-amperes, a significant current that would quickly discharge a small battery. The battery drain problem can be solved by scheduling the on time of the LED(s), both by driving the LED(s) with very narrow current pulses, and by optionally scheduling the operation of the entire optical pulse detect system. For example, it is possible to detect heartbeats on a duty cycle basis such as five seconds on and fifteen to twenty seconds off. This would allow the detection of about five heartbeats during the on time, and delay the worse case detection by only fifteen to twenty seconds. It is therefore possible to extend battery life by minimizing on time of the LED(s).

In an embodiment worn on a patient's wrist, the optical sensor 201 can use scattered light transmitted into the wrist from the bottom of the wrist worn portion (e.g., watch) of the device, or can use transmitted light through the finger tip by means of a short cable connected to a finger clip. In the transmitted light case, the LED(s) and the optical sensor 201 are on opposite sides of the fingertip while in the scattered light case the optical sensor and transmitter are on the same side of the wrist.

The physiological parameter measuring device 40 further comprising a temperature sensor 211. Such a temperature sensor 211 can be built into the bottom of the housing to sense wrist temperature. Temperature sensor 211 may comprise a programmable alarm function with both upper and lower temperature alarm points, such as a Maxim DS18S20. In some embodiments, the temperature sensor 211 would have both low power operation, and automatic operation unloading the processor 206 from background tasks, and allowing the processor 206 to maintain its lowest power mode for as long as possible. Although temperature alone cannot be used to sense fibrillation, it is a commonly recorded physiological parameter physicians often want to see if the device is used for physiological recording. Similarly, the device and software can be extended so that the device can calculate $SpO_2$ and record physiological parameters such as oxygen saturation values and heart rate in addition to being a warning device. In the $SpO_2$ case, multiple LEDs are used, both infrared and visible.

The ECG sensor 204 is for monitoring the electrical activity of the patient's heart over a period of time. The ECG sensor 204 illustrated in this Figure comprising an ECG amplifier 212, a first ECG electrode 203, a second ECG electrode 203', and analog pre-processing module 205. The ECG amplifier 212 can be of conventional design, can be optimized for low power use, for instance by utilizing micro-power operational amplifiers where possible. The analog pre-processing module 205 can include filters to both keep the ECG baseline constant, and anti-aliasing filters for the A-D conversion step. While such a configuration of an ECG sensor is disclosed here, a skilled artisan will be able to select an appropriate structure and configuration for an ECG sensor in a particular embodiment based on various considerations, including the intended use of the medical system, the intended arena within which the medical system will be used, and the equipment and/or accessories with which the ECG sensor is intended to be used, among other considerations.

The touch switch 207 has an interface 208. The touch switch 207 may be incorporated as a capacitive switch, such as a Rohm BU21010MUV. A capacitive switch senses a finger touch, but is not mechanical for easier waterproofing and operation. The touch switch 207 can be used to sense gestures, such as short touch, long touch, and finger motion, which can be used to both activate and inhibit alarms as already described. Alternatively, touch switch 207 could comprise a touch screen on the front surface of the physiological parameter measuring device 40.

Low power sensor 209 can comprise a motion sensor, such as an accelerometer having a low current operation, such as a Freescale MMA 8450Q semiconductor. The motion sensor can have built-in motion detecting features that run automatically, unloading the processor 206 from background tasks.

In some embodiments, the low power sensor 209 includes automatic detection of free-fall and transient detection, to detect a fall pattern which would be a zero-G interval, the fall, followed by a transient, the impact. Such a low power sensor 209 able to alert the processor 206 and/or one or more of the other sensors to check for heart activity in case the fall is from cardiac arrest.

The motion sensor can perform two additional functions; during times of extreme motion, the system can be placed into a lower power state by turning off the LEDs—a patient in ventricular fibrillation will not be exhibiting sustained extreme motion. It is also possible to use the motion sensor to sense convulsions that often occur during anoxia and could mimic a heartbeat signal. Thus ventricular fibrillation can be a lack of pulse and lack of motion, or a lack of pulse with a brief lack of motion followed by convulsion pattern then lack of motion again. Thus, the addition of the motion sensor saves power and extends battery life and also increases the specificity of the physiological parameter sensor.

The physiological parameter measuring device 40 may also comprise a communication module 210 for allowing the physiological parameter measuring device 40 to make a wireless connection with other devices. For instance, the communication module 210 may utilize the Bluetooth wireless technology standard and an antenna for exchanging data over short distances with another device.

The physiological parameter measuring device 40 includes a processor 206. The processor 206 connecting with the sensors, and contains algorithms for detecting cardiac problems. Such algorithms are known in the art, for example a method for detecting ventricular fibrillation (VF) from an ECG is disclosed in U.S. Pat. Nos. 4,184,493 and 4,475,551 by Langer. The method described in those patents can be implemented in software.

The optical sensor 201 can be asleep and be awakened by the lack of motion from the low power sensor 209 (e.g., accelerometer or other motion sensor). As another example, the optical sensor 201 could be awakened by output of ECG electrodes 203 and/or 203'. The exact sequence of sensors running and waking other is programmable and tailored to the specific patient.

Figure 4:
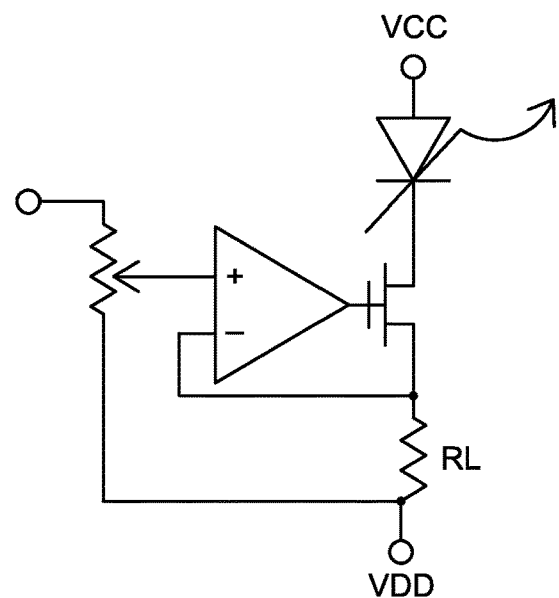
FIG. 4 is a schematic representation of one embodiment of an optical sensor.
Figure 5:
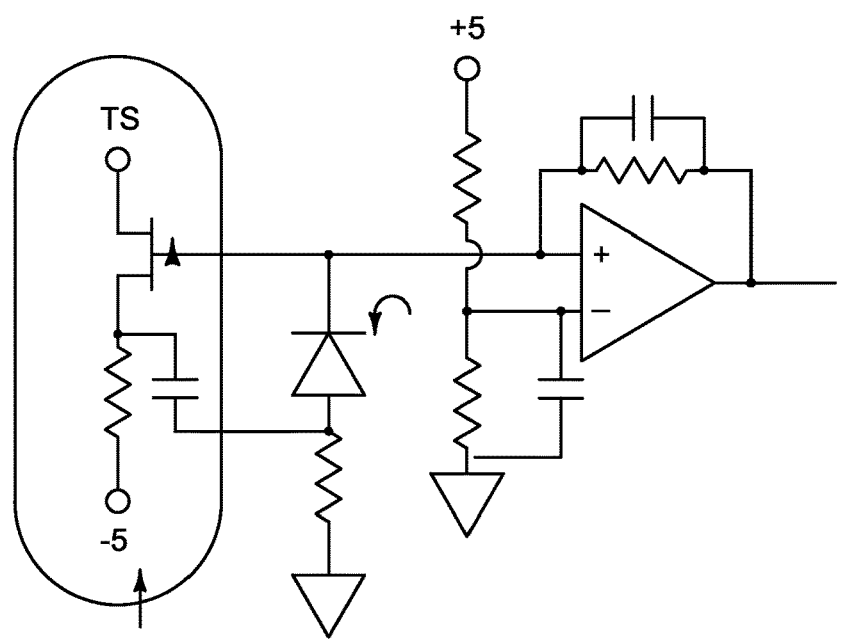
FIG. 5 is a schematic representation of an LED driver.

FIGS. 4 and 5 illustrate one embodiment of an optical sensor 201. In FIG. 4, the optical sensor's output is examined for heart beat pulses by a correlation method. During a training phase, a pulse template is built by looking for peaks in the pulse waveform and averaging data points around those peaks that meet certain criteria. The average template is stored in the device. After the training phase as data comes in from the optical sensor, the data continues to be examined for peaks. Each peak is cross-correlated with the template to see if a beat is present and the pattern is examined for intervals. An absence of detected beats, or an interval pattern that is not normal, will trigger an alarm. This method has been chosen since correlation is very effective in detecting a signal in noise.

Referring now to FIG. 5, illustrated is an LED driver with a programmable current drive. Preferably, the current is set by a programmable resistor, such as Microchip MMM and a PIO pin of the microprocessor. The preferable current drive would not require a DAC in the microprocessor and would have a lower current. Proper selection of the operational amplifier allows it to operate at the negative rail at low current. Thereby, the overall current draw is reduced to almost that of the LED current. Also illustrated is a high-speed trans-conductance amplifier used to change the photodiode current into a voltage for the microprocessor's analog to digital converter. The JFET is included to allow even higher speed operation by bootstrapping. Thus, the LED driver and photo amplifier have been designed with very narrow light pulses in mind, thereby minimizing current draw.

As discussed above, one embodiment of the system comprises a wrist-worn housing containing at least a portion of the components of the system, for instance the optical sensor. In other embodiments, the optical sensor may be separate from the wrist-worn housing—for example, the optical sensor could be incorporated in to a finger ring worn on a patient's finger and connected by a wire to the wrist-worn housing.

Figure 6:
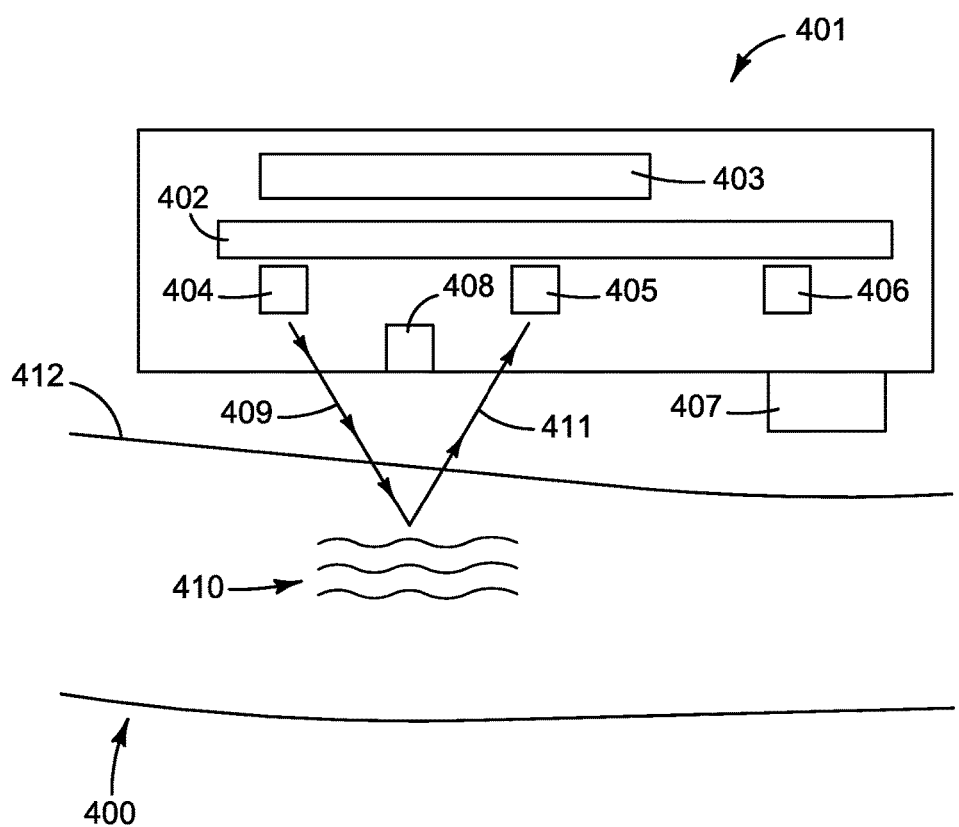
FIG. 6 is a diagram illustration of one embodiment of a wrist worn medical system.

FIG. 6 illustrates an embodiment of a wrist worn medical system 401. The wrist worn medical system 401 comprises a transparent window on the top and bottom surfaces. The top window allows the user to see information displayed on a display 403, such as an OLED display. The bottom window allows light to be transmitted into the skin 412. The transmitted light beam 409 is generated by LED 404. The light beam 409 enters the patient's skin at the wrist, and interacts with blood in the tissue 410 of the patient's skin. The scattered light 411 is detected by photodiode 405. Light passing directly from the LED 404 to the photodiode 405 is prevented by optical barrier 408 which is placed as close as possible to the bottom transparent window. As already discussed, the scattered light intensity will contain a pulsatile component caused by variations in arterial blood in the tissue pool synchronized to the heartbeat.

All components can be mounted on a printed circuit board 402, including an accelerometer 406. Some components, such as the LED and the photodiode, may be mounted on the PCB surface facing the wrist worn medical system 401 (bottom surface); while other components, such as the display 403, may be mounted on the top surface. Not illustrated are other components and modules, e.g., the processor, can also be mounted on the PCB.

On the bottom surface of the wrist worn medical system 401, directly exposed to the patient's skin is also mounted ECG electrode 407 which provides one signal to the ECG processing circuit. This ECG electrode 407 is insulated from the wrist worn medical system 401 case and may be composed of conductive plastic or in the alternative, a capacitive electrode. A capacitive electrode is one where a very thin insulating film is placed on the electrode's surface facing the patient's skin and is known to those skilled in the art.

Figure 7:
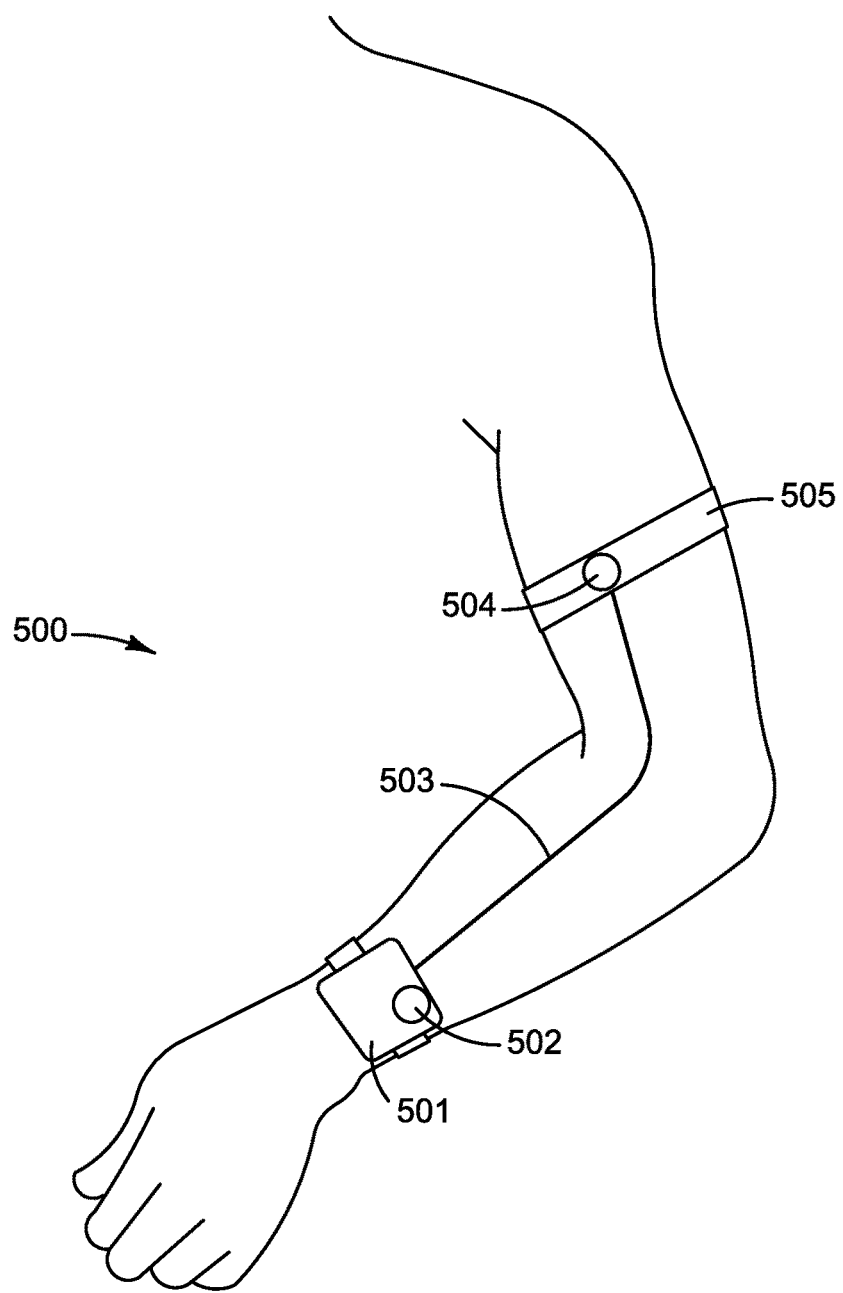
FIG. 7 is a diagram illustration of another embodiment of a wrist worn medical system.

FIG. 7, illustrates another embodiment of the medical system 500. The medical system 500 is illustrated as a wrist worn medical system 501. Light energy is being transmitted from the bottom of the wrist worn medical system 501 was already discussed. On the top surface of the wrist worn medical system 501 is both the transparent window allowing visualization of the display, and a cancel button area 502 of the top surface which allows cancellation of the transmitted alarm if the patient is conscious. The top surface cancel button area 502 may be implemented as a touch screen.

Flexible wire 503 exits the wrist worn medical system 501 to connect with and upper arm ECG electrode 504 attached to an arm band 505. ECG signal are measured as a potential difference between two electrodes. Here, as discussed above, one electrode is on the bottom surface of the wrist worn medical system 501, while the other electrode is somewhere else on the forearm or upper arm. The spacing between the electrodes will affect the quality of the ECG signal with larger spacings providing a better ECG signal. Other ECG electrode placements are possible, such as a separate ECG module worn on a chest strap.

The medical system also contains an audio alert device and a switch, preferably a capacitive switch, on the front face of the watch. If an alert condition is sensed, the audio alert is optionally sounded before the actual alert is transmitted. The patient has the opportunity to delay or cancel the alert by engaging and holding the switch. If the alert is real, the patient will become unconscious and release the switch and the event is transmitted normally. In a non-alarm condition, the switch can be pushed to initiate a manually triggered help request. The user presses on the switch area and after several seconds of constant activation the alarm is sent. The delay is provided to minimize accidental activation.

Figure 8:
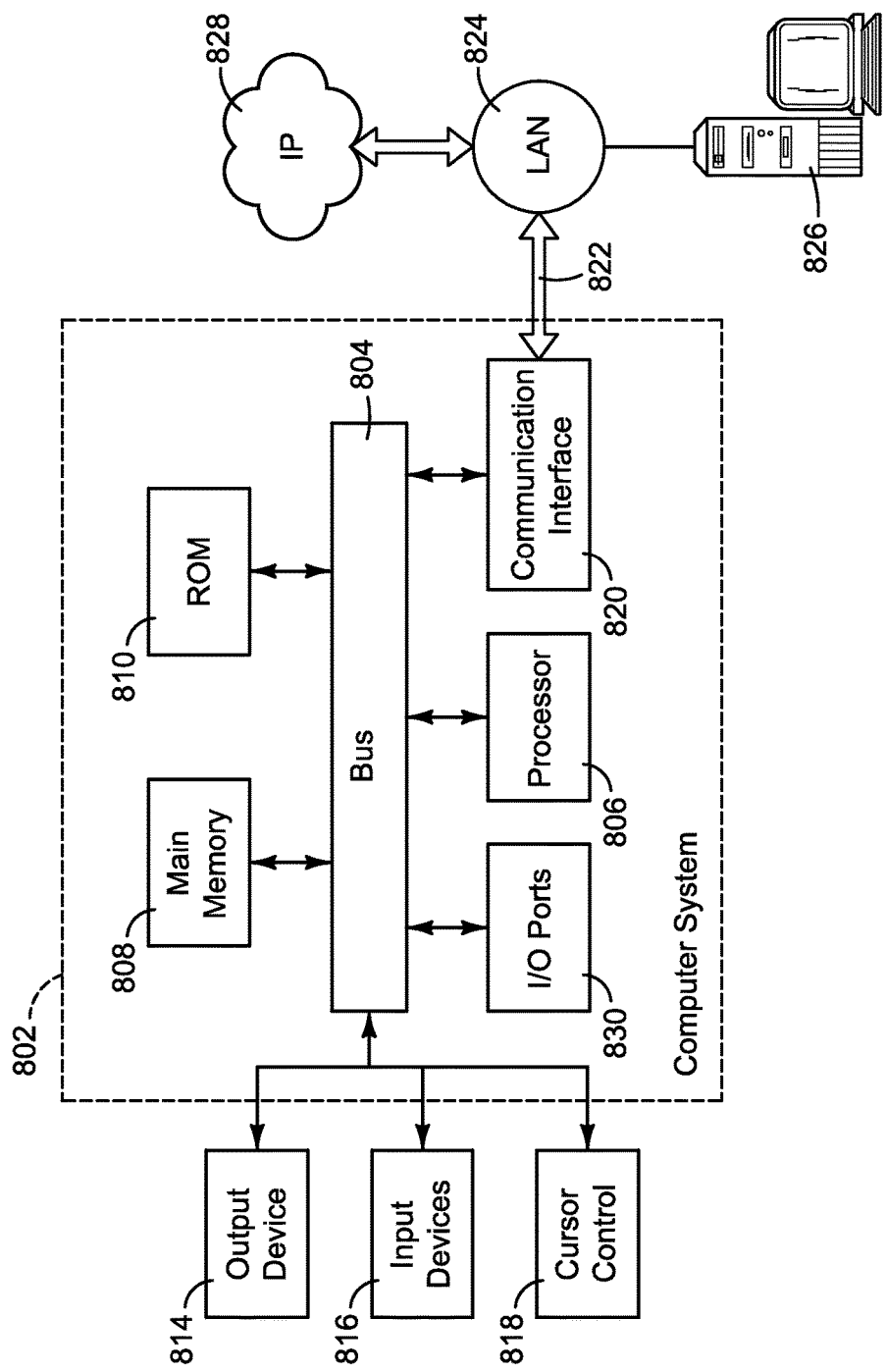
FIG. 8 is a block diagram illustrating on embodiment of a master control system.

FIG. 8 is a block diagram illustrating on embodiment of a master control system 802 upon which the medical system for sensing a physiological state requiring defibrillation in a patient may be implemented. The master control system 802 may be any one of a microprocessor-based system, a personal computer system, a work station computer system, a lap top computer system, an embedded controller system, a digital signal processor-based system, a hand held device system, a patient worn system, a personal digital assistant (PDA) system, a wireless system, a wireless networking system, etc. In the embodiments illustrated in the Figures, the master control system 802 is a microprocessor-based system.

The master control system 802 includes a bus 804 or other communication mechanism for communicating information, and a processor 806 coupled with the bus 804 for processing the information. The master control system 802 may also include a main memory 808 coupled to bus 804 for storing information and instructions to be executed by processor 806. The main memory 808 may be used for storing temporary variables or other intermediate information during execution of instructions to be executed by processor 806. Master control system 802 may further include a read only memory (ROM) 810 or other static storage device (e.g., programmable ROM (PROM), erasable PROM (EPROM), and electrically erasable PROM (EEPROM)) coupled to bus 804 for storing static information and instructions for processor 806.

The master control system 802 also includes input/output ports 830 to couple the master control system 802 to external devices, such sensors and ECG electrodes. Such coupling may include direct electrical connections, wireless connections, networked connections, etc., for implementing automatic control functions, remote control functions, etc.

The master control system 802 may be coupled via bus 804 to an output device 814 (e.g., liquid crystal display (LCD), light emitting diode (LED) display, voice synthesis hardware, voice synthesis software, speaker) for displaying and/or providing information to a patient, health care provider, or other person. The output device 814 may be controlled by a display card, graphics card, sound card, or other modules.

The master control system 802 can include one or more input devices 816, including but not limited to push buttons, keyboards, and a cursor control 818, such as a touch screen, for communicating information and command selections to the processor 806. Such command selections can also be implemented via voice recognition hardware and/or software functioning as the input devices 816. The cursor control 818, for example, is a mouse, a trackball, cursor direction keys, touch screen display, optical character recognition hardware and/or software, etc., for communicating direction information and command selections to processor 806 and for controlling cursor movement on the output device 814 (e.g., a display).

The master control system 802 performs a portion or all of the processing steps of the medical system in response to processor 806 executing one or more sequences of one or more instructions contained in a memory, such as the main memory 808. In alternative embodiments, hard-wired circuitry may be used in place of or in combination with software instructions. Thus, embodiments are not limited to any specific combination of hardware circuitry and software.

The master control system 802 also includes a communication interface 820 coupled to bus 804. Communication interface 820 provides a two-way data communication coupling to a network link 822 that may be connected to, for example, a local network 824. For example, communication interface 820 may be a network interface card to attach to any packet switched local area network (LAN), or to a personal area network (PAN) using a convenient protocol, including but not limited to the ZIGBEE protocol, the ANT protocol, and Bluetooth. Wireless links may also be implemented via the communication interface 820. In any such implementation, communication interface 820 sends and receives electrical, electromagnetic or optical signals that carry digital data streams representing various types of information.

Network link 822 typically provides data communication through one or more networks to other data devices. For example, network link 822 may provide a connection to a computer 826 through local network 824 (e.g., a LAN) or through equipment operated by a service provider, which provides communication services through a communications network 828. The master control system 802 can transmit notifications and receive data, including program code, through the network(s), network link 822 and communication interface 820.

Another embodiment is a medical system for sensing a physiological state requiring defibrillation in a patient, the system comprising: a low power sensor, said low power sensor generating a baseline signal relating to a physiological status of said patient; physiological parameter measuring device comprising at least one higher power sensor configured to output at least one physiological parameter signal indicative of at least one physiological parameter of said patient; a processor, the processor assessing the baseline signal, the processor implementing at least in part a control logic for determining if the physiological status is outside predetermined threshold boundaries, whereupon determining that the physiological status is outside said threshold boundaries, the control logic is configured to enable said at least one higher power sensor to acquire a physiological parameter signal indicative of at least one physiological parameter of said patient; and the processor assessing the at least one physiological parameter signal to determine whether a physiological state requiring defibrillation in a patient is present.

Alternatively, the low power sensor comprises a motion sensor, and wherein said baseline signal comprises a motion signal relating to an activity level of the patient. Alternatively, whereupon determining that a physiological state requiring defibrillation in a patient is present, the processor outputs an alarm signal to an alarm module, alarm module for generating an alarm. Alternatively, the low power sensor comprises an ECG sensor. Alternatively, the medical system further comprises an external, free-standing defibrillator for use by a third party in response to said alarm. Alternatively, the physiological parameter sensor is selected from the group consisting of an ECG sensor, a blood oxygen sensor, heart pulse sensor, a pulse oximeter, and a temperature sensor. Alternatively, at least part of the physiological parameter measuring device is disposed in a housing worn on at least one of the patient's wrists, or in an housing attached to a chest strap worn by the patient. Alternatively, the alarm module comprises an amplifier and a speaker, and said alarm signal is an audible alarm indicating to a third party that the patient is experiencing emergency level physiological parameters and an external free-standing defibrillator needs to be utilized on said patient.

Alternatively, the alarm module further comprises a communication device for communicating at least one of said signals to a central receiving station; said central receiving station receiving said signal(s), said central receiving station comprising an emergency level verification system for verifying said signal(s) to determine if emergency level physiological parameters are present, said central receiving station further comprising a confirmation signal generator for generating a confirmation signal upon the verification of the presence of emergency level physiological parameters; and a notification device configured to receive said confirmation signal, said notification device also configured for automatically providing notice of the detection of an emergency-level physiological parameter to a third party proximal to said individual, said notification device indicating to said third party that the individual is experiencing emergency level physiological parameters and the external free-standing defibrillator needs to be utilized on said individual. Alternatively, the master control system has an active mode, a sleep mode, and an interrupt system, wherein said low power sensor implements a control logic for determining if the physiological status is outside predetermined threshold boundaries, whereupon determining that the physiological status is outside said threshold boundaries, the control logic is configured to issue an interrupt signal to the master control system, triggering the master control system to enter into the active mode.

In another embodiment, the medical system is for sensing a physiological state requiring defibrillation in a patient, said system comprising: a motion sensor, said motion sensor generating a motion signal relating to an activity level of the patient; physiological parameter measuring device comprising at least one physiological parameter sensor configured to output at least one physiological parameter signal indicative of at least one physiological parameter of said patient; a processor, the processor assessing the motion signal, the processor implementing at least in part a control logic for determining when the patient's activity level is below a threshold level, whereupon determining that the patient's activity level is below said threshold level, the control logic is configured to wake up said at least one physiological parameter sensor to acquire a physiological parameter signal indicative of at least one physiological parameter of said patient; the processor assessing the at least one physiological parameter signal to determine whether a physiological state requiring defibrillation in a patient is present, whereupon determining that a physiological state requiring defibrillation in a patient is present, the processor outputs an alarm signal to an alarm module; and said alarm module for creating an alarm upon receipt of an alarm signal.

Alternatively, the medical system further comprising an external, free-standing defibrillator for use by a third party in response to said alarm. Alternatively, the physiological parameter sensor is selected from the group consisting of an ECG sensor, a blood oxygen sensor, heart pulse sensor, a pulse oximeter, and a temperature sensor. Alternatively, at least part of the physiological parameter measuring device is disposed in a housing worn on at least one of the patient's wrists, or in a housing attached to a chest strap worn by the patient. Alternatively, the alarm module comprises an amplifier and a speaker, and said alarm signal is an audible alarm indicating to a third party that the patient is experiencing emergency level physiological parameters and an external free-standing defibrillator needs to be utilized on said patient.

Alternatively, the alarm module further comprises a communication device for communicating at least one of said signals to a central receiving station; said central receiving station receiving said signal(s), said central receiving station comprising an emergency level verification system for verifying said signal(s) to determine if emergency level physiological parameters are present, said central receiving station further comprising a confirmation signal generator for generating a confirmation signal upon the verification of the presence of emergency level physiological parameters; and a notification device configured to receive said confirmation signal, said notification device also configured for automatically providing notice of the detection of an emergency-level physiological parameter to a third party proximal to said individual, said notification device indicating to said third party that the individual is experiencing emergency level physiological parameters and the external free-standing defibrillator needs to be utilized on said individual.

Alternatively, the medical system further comprises a housing and a wrist strap connected to said housing, wherein said motion sensor, at least one of said physiological parameter sensors, and said processor are located within said housing. Alternatively, the motion sensor is an accelerometer.

Another embodiment comprises a method of sensing a physiological state requiring defibrillation in a patient comprising: placing a physiological parameter sensor in a low power state; utilizing a motion sensor to generate a motion signal relating to an activity level of the patient; assessing the motion signal and determining if the patient's activity level is below a threshold level; whereupon determining that the patient's activity level is below said threshold level, waking up said physiological parameter sensor, said physiological parameter sensor sensing at least one physiological parameter signal indicative of at least one physiological parameter of said patient; and assessing the at least one physiological parameter signal to determine whether a physiological state requiring defibrillation in a patient is present; and whereupon determining that a physiological state requiring defibrillation in a patient is present, outputting an alarm signal to an alarm module to create an alarm. Alternatively, the method further comprises in response to said alarm, applying an AED to the patient.

The foregoing detailed description provides exemplary embodiments of the medical system and method, and includes the best mode for practicing the medical system. The description and illustration of these embodiments is intended only to provide examples of the medical system and method, and not to limit the scope of the medical system and its method, or its protection, in any manner.

What is claimed is:

1. A medical system for sensing a physiological state requiring defibrillation in a patient, the system comprising:
   a baseline signal sensor to generate a baseline signal relating to an activity level of a patient over time, the activity level determined based on one or more of motion of the patient or electrical activity of a heart of the patient;
   a physiological parameter measuring device comprising at least one parameter sensor having a higher power consumption than the baseline signal sensor, the at least one parameter sensor having a low power state during which the physiological parameter measuring device sleeps and a higher power state during which the at least one parameter sensor outputs at least one physiological parameter signal indicative of at least one physiological parameter of the patient; and
   a processor configured to:
      control the at least one parameter sensor to enter the higher power state to output the physiological parameter signal responsive to a trigger event determined from the baseline signal, the trigger event comprising one or more of reduction of the motion of the patient or reduction of the electrical activity of the heart of the patient below predetermined threshold boundaries over time; and
      assess the at least one physiological parameter signal to determine whether a physiological state requiring defibrillation in a patient is present.

2. The medical system of claim 1, wherein the baseline signal sensor comprises a motion sensor.

3. The medical system of claim 1, whereupon determining that a physiological state requiring defibrillation in a patient is present, the processor outputs an alarm signal to an alarm module, alarm module for generating an alarm.

4. The medical system of claim 3, further comprising an external, free-standing defibrillator for use by a third party in response to said alarm.

5. The medical system of claim 3, wherein said alarm signal is an audible alarm indicating to a third party that the patient is experiencing emergency level physiological parameters and an external free-standing defibrillator needs to be utilized on said patient.

6. The medical system of claim 3, wherein said alarm module further comprises a communication device for communicating at least one of said signals to a central receiving station; said central receiving station receiving said signal(s), said central receiving station comprising an emergency level verification system for verifying said signal(s) to determine if emergency level physiological parameters are present, said central receiving station further comprising a confirmation signal generator for generating a confirmation signal upon the verification of the presence of emergency level physiological parameters; and a notification device configured to receive said confirmation signal, said notification device also configured for automatically providing notice of the detection of an emergency-level physiological parameter to a third party that the individual is experiencing emergency level physiological parameters and the external free-standing defibrillator needs to be utilized on said individual.

7. The medical system of claim 1, wherein said baseline signal sensor comprises an ECG sensor.

8. The medical system of claim 1, wherein said parameter sensor is selected from the group consisting of an ECG sensor, a blood oxygen sensor, a heart pulse sensor, and a pulse oximeter.

9. The medical system of claim 1, wherein at least part of the physiological parameter measuring device is disposed in a housing worn on at least one of the patient's wrists, or in a housing attached to a chest strap worn by the patient.

10. The medical system of claim 1, further comprising a battery for supplying power.

11. A medical system for sensing a physiological state requiring defibrillation in a patient, the system comprising:
    a low power sensor including control logic configured to generate an interrupt signal upon determining that a physiological status of a patient, as measured by the low power sensor, is outside predetermined threshold boundaries;
    a physiological parameter measuring device comprising at least one parameter sensor, the at least one parameter sensor having a higher power consumption than the low power sensor, the at least one parameter sensor having a low power state during which the physiological parameter measuring device sleeps and a higher power state during which the at least one parameter sensor outputs at least one physiological parameter signal indicative of at least one physiological parameter of the patient; and
    a master control system configured to:
       control the at least one parameter sensor to enter the higher power state to output the physiological parameter signal responsive to the interrupt signal generated by the low power sensor; and
       assess the at least one physiological parameter signal to determine whether a physiological state that requires defibrillation in the patient is present;

wherein:
the master control system has an active mode and a sleep mode; and
the interrupt signal is configured to trigger the master control system to enter into the active mode.

* * * * *